United States Patent
Bewick-Sonntag et al.

(10) Patent No.: US 6,417,424 B1
(45) Date of Patent: *Jul. 9, 2002

(54) BREATHABLE ABSORBENT ARTICLES HAVING ODOR CONTROL

(75) Inventors: Christopher Philip Bewick-Sonntag, Pescara; Giovanni Carlucci, Chieti; Achille Di Cintio; Carmine Cimini, both of Pescara, all of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,300

(22) PCT Filed: Jun. 17, 1997

(86) PCT No.: PCT/US97/10589

§ 371 (c)(1),
(2), (4) Date: Dec. 11, 1998

(87) PCT Pub. No.: WO97/48362

PCT Pub. Date: Dec. 24, 1997

(30) Foreign Application Priority Data

Jun. 17, 1996 (EP) .............................................. 96830343
Aug. 1, 1996 (EP) .............................................. 96112404

(51) Int. Cl.⁷ .......................... A61F 13/15; A61F 13/20
(52) U.S. Cl. ........................................ 604/367; 604/359
(58) Field of Search .............................. 604/358, 359, 604/378, 385.01, 385.23, 367

(56) References Cited

U.S. PATENT DOCUMENTS

| | | |
|---|---|---|
| 3,340,875 A | 9/1967 | Dudley et al. |
| 3,812,044 A | 5/1974 | Conner et al. |
| 3,929,135 A | 12/1975 | Thompson |
| 4,151,240 A | 4/1979 | Lucas et al. |
| 4,289,513 A | 9/1981 | Brownhill et al. |
| 4,319,868 A | 3/1982 | Riemersma et al. |
| 4,324,426 A | 4/1982 | Michelson |
| 4,341,216 A | 7/1982 | Obenour |
| 4,343,314 A | 8/1982 | Stramek |
| 4,356,190 A | 10/1982 | Kraskin |
| 4,591,523 A | 5/1986 | Thompson |
| 4,637,819 A | 1/1987 | Ouellette et al. |
| 4,713,068 A | 12/1987 | Wang et al. |
| 5,407,442 A * | 4/1995 | Karapasha .................. 604/359 |
| 5,429,628 A | 7/1995 | Trinh et al. |

FOREIGN PATENT DOCUMENTS

| | | |
|---|---|---|
| EP | 348 978 A2 | 1/1990 |
| EP | 510 619 A1 | 10/1992 |
| EP | 705 583 A1 | 4/1996 |
| EP | 705 584 A1 | 4/1996 |
| EP | 710 471 A1 | 5/1996 |
| EP | 710472 A1 | 5/1996 |
| WO | WO 81/01643 A1 | 6/1981 |
| WO | WO 91/11977 A1 | 8/1991 |
| WO | WO 91/12029 | 8/1991 |
| WO | WO 91/12030 A1 | 8/1991 |
| WO | WO 94/22500 A1 | 10/1994 |
| WO | WO 94/25077 A1 | 11/1994 |
| WO | WO 96/06589 A1 | 3/1996 |

* cited by examiner

Primary Examiner—John G. Weiss
Assistant Examiner—Michelle Kidwell
(74) Attorney, Agent, or Firm—Matthew P. Fitzpatrick; Kirsten K. Stone

(57) ABSTRACT

The present invention relates to absorbent articles in particular sanitary napkins with improved comfort, particularly by the incorporation of breathable backsheets while maintaining protection level performance and having an improved odour control performance. This has been achieved by the selection of individual elements for the absorbent article including an odour control system which meet specified requirements, which are then joined such that the absorbent article meets specific criteria in terms of comfort and protection and provides improved odour control performance.

21 Claims, No Drawings

BREATHABLE ABSORBENT ARTICLES HAVING ODOR CONTROL

FIELD OF THE INVENTION

The present invention relates to absorbent articles in particular sanitary napkins and panty liners which are breathable and have an improved odour control system.

BACKGROUND OF THE INVENTION

The primary consumer needs which underlie development in the absorbent article field, in particular catamenials is the provision of products providing both a high protection and comfort level.

One means for providing consumer comfort benefits in absorbent articles is by the provision of breathable products. Breathability has typically concentrated on the incorporation of so called 'breathable backsheets' in the absorbent articles. Commonly utilised breathable backsheets are microporous films and apertured formed films having directional fluid transfer as disclosed in for example U.S. Pat. No. 4,591,523. Both these types of breathable backsheets are vapour permeable allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use, commonly associated with the presence of an apertured formed film or film like topsheet, particularly over extended periods of time. This is a result of topsheets designed to achieve a clean and dry appearance. These topsheets tend to be smooth thereby minimising the build up of fluid on the surface of the topsheet. However, these benefits are achieved at the expense of comfort, particularly under hot and humid conditions, when due to their smooth surface texture they tend to become sticky to the skin.

However, the main drawback associated with the use of breathable backsheets in absorbent articles is the negative effect on the protection level performance, by leakage known as wet through onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the product is utilised during physical exertion, or for heavy discharge loads or over extended periods of time. Thus, whilst the incorporation of breathable backsheets in absorbent articles is highly desirable from a comfort standpoint, since the primary role of a backsheet still remains the prevention of liquid leakage, such breathable backsheets cannot be satisfactorily incorporated into products.

The problem of wet through onto users garments due to the incorporation of such breathable backsheets in absorbent articles has indeed also been recognised in the art. Attempts to solve the problem have mainly resided in the use of multiple layer backsheets such as those illustrated in U.S. Pat. No. 4,341,216. Similarly European patent application no. 710 471 discloses a breathable backsheet comprising an outer layer of a gas permeable, hydrophobic, polymeric fibrous fabric and an inner layer comprising an apertured formed film having directional fluid transport. The backsheet construction preferably has no liquid transport/wet through under certain specified test conditions. Also European patent application no. 710 472 discloses a breathable backsheet consisting of at least two breathable layers which are unattached to one another over the core area. The backsheet construction preferably has no liquid transport/ wet through under certain specified test conditions.

U.S. Pat. No. 4,713,068 discloses a breathable clothlike barrier for use as an outer cover for absorbent articles. The barrier comprises at least 2 layers, a first layer having a specified basis weight, fibre diameter and pore size and a second layer comprising a continuous film of poly (vinyl alcohol) having a specified thickness. The barrier also has a specified water vapour transmission rate and level of impermeability.

However, none of the above proposed solutions have been able to provide a fully satisfactory solution to the problem of breathable backsheet wet through under all conditions. Furthermore, another problem associated with the exemplified multi layer backsheets is an increase in total thickness of the product and a reduction in the flexibility, both of which result in a consumer noticeable reduction in product comfort.

An alternative proposed solution to the problem of breathable backsheet wet through relates to the improvement of the absorbent material such that little or no liquid comes into contact with the backsheet, thereby preventing wet through. This is typically achieved by increasing the amount of absorbent material in the article. However, this results in an absorbent article which is extremely thick which is highly undesirable from a consumer comfort standpoint. Hence, the absorbent article whilst having the required protection level and still maintaining some comfort benefits by the presence of the breathable backsheet, suffers from a lack of comfort from a different source, in this case the increased dimensions of the article.

In addition the above solution also results in a reduction in the flexibility of the article, particularly evident as an increase in the cross section stiffness. It is however also well established that in order to be comfortable for the wearer absorbent articles need to be cross sectionally flexible. It is believed that the more cross sectionally flexible an absorbent article is, the less will it be noticeable to the wearer. Thus flexibility is another highly desirable comfort requirement of modern absorbent articles.

EPO 705 583 and EPO 705 584 propose longitudinally flexible absorbent articles which are vapour permeable. However, the exemplified absorbent articles are typically very thin and do not address the absorbency capacity of the article or the problem of wet through.

Consequently, as the incorporation of breathable backsheets in absorbent articles results in reduction of the protection level, further desirable product comfort modifications such as reducing the thickness of the product and improving the flexibility of the product which would further acerbate the problem may not be incorporated in the absorbent article.

Thus, there exists a dichotomy in the means available to provide increased consumer comfort in absorbent products and acceptable protection levels. It is therefore an objective of the present invention to provide an absorbent article having improved comfort, by the provision of breathability throughout the absorbent article and which maintains an acceptable level of protection.

It has now been found that this objective may be achieved by the provision of an article whose individual elements must meet certain key functional parameter criteria in terms of comfort provision and/or protection such as the backsheet wet through/liquid permeability, the topsheet dryness, the core caliper and core vapour or vapour/air permeability.

Furthermore, these elements are combined such that the resultant product, in addition to these individual elements, meets overall criteria such that it has a certain dryness index and sensory index. The present invention has identified the key components which affect the principle comfort requirements of flexibility, breathability, dryness and caliper and the key components of protection such as liquid retention/wet through and rewet. Surprisingly, it has been found that the specific combination of these components, provides an article delivering both high protection levels as well as high comfort to the consumer. In particular it is believed that breathability must be considered in terms of total article breathability in addition to the backsheet breathability in order to provide a truly breathable product.

However, a new problem has now been identified which is related to the effective incorporation of breathable backsheets in absorbent articles so as to provide breathable absorbent articles. This problem concerns the perceived increased ease of detection of malodourous compounds within the absorbent article by at least a proportion of users of these breathable products.

Malodourous compounds typically present in absorbent articles originate from a number of sources. Firstly, the components of the fluid discharge such as urine, perspiration, menstrual fluid and blood may themselves contain odourous compounds. Secondly, malodourous compounds may be generated as a result of the degradation of the components of the fluid discharge. Thus there are a wide range of compounds which may be present at some time during the use of an absorbent article which have an associated malodour. These compounds include fatty acids, ammonia, amines, sulphur containing compounds and ketones and aldehydes and numerous derivatives thereof.

It is believed that due to the very nature of a breathable absorbent products, malodourous compounds contained therein may, similar to air and vapour, be more readily exchanged with the environment. Hence, the malodourous compounds are able to escape from the article and are dissipated into the surroundings. Consequently, it is at least perceived by a number of potential users of these products that malodourous compounds are more easily detectable from breathable absorbent articles than from non breathable absorbent articles. The presence and detection of malodourous compounds from absorbent articles is however highly undesirable and may cause the wearer of these products extreme embarrassment and thus, the prevention of their detection is highly desirable.

It is thus an objective of the present invention to provide an absorbent article which is breathable and provides the desired level of protection and which reduces and preferably prevents the detection of odourous compounds emanating therefrom in use.

It has now been found that the combination of breathable absorbent articles with an odour control system provides not only the associated benefits of a truly breathable product as described herein above, but also provides a more effective odour control system. In particular, it has been surprisingly observed that the amount of odour control system incorporated into such breathable articles may be reduced whilst still maintaining the same level of odour control as in a non breathable absorbent article.

It is believed that the performance benefit of the odour control system is due to an interaction of the breathable environment of the absorbent article and the odour control agent contained therein. This believed to be due to a number of factors.

Firstly, the breathability of the article results in increased movement of the volatile malodourous compounds. Hence, the amount of actual physical contact between these compounds and the odour control agents increases. Contact between the odour control agents and the malodourous compounds is usually required in order to effective combat the odourous compound. Frequently large quantities of odour control agent is required in absorbent article in order to be effective because the agents does not necessarily contact the malodourous compounds. In the present invention the effectiveness of the odour control agent is significantly increased and the full capacity of the odour control agents can be utilised.

Secondly, due to the breathability of the article, which reduces the hot humid and anaerobic environment between the skin of the wearer and the surface of the absorbent article, the growth of microorganisms is reduced. Microorganisms are also known to be responsible for the generation of odourous compounds.

Thirdly, the reduction in the hot, humid and occlusive environment between the vicinity of the skin of the wearer and the article itself also reduces the tendency of the wearer to perspire. Consequently, the amount of associated perspiration related odour will be reduced. Thus, the breathability of the article actually reduces the amount of odour generated within the absorbent article. As a result the odour control system works more effectively on the remaining odourous compounds present in the article.

An additional benefit of the present invention is that the combination of breathability and odour control leads to an improvement in the overall dryness of the product. The breathability of the article allows for the evaporation of fluid from the article, and also as indicated above a reduction in the amount of perspiration generated by the wearer of the product and thus a reduction in hot and sweaty feelings often associated with the presence of topsheets designed to retain a clean and dry surface. The article therefore needs to retain less fluid and can do so more effectively. Furthermore the odour control agents are also typically able to absorb fluid and thereby improve dryness.

SUMMARY OF THE INVENTION

The present invention relates to a breathable disposable absorbent article having an improved odour control comprising the following elements:

a liquid pervious topsheet, an absorbent core and a breathable backsheet, said absorbent core being positioned intermediate said topsheet and said backsheet, said topsheet, core and backsheet each comprising at least one layer. The topsheet has a liquid retention of less than 0.22 g for a 2.0 g load in the topsheet liquid retention test. The core has a caliper of less than 12 mm and has a vapour permeability of at least 200 g/m$^2$/24 hrs. as defined in the vapour permeability test. The breathable backsheet has a liquid permeability of less than 0.3 g for a 7 ml. load as defined in the liquid permeability test. The elements are joined such that said absorbent article has a dryness index of greater than 0.5 and a sensory index of greater than 50. Furthermore, the disposable absorbent article also comprises an odour control system preferably positioned within the absorbent core, which in combination with the specific construction of the absorbent article provides improved odour control performance.

DETAILED DESCRIPTION OF THE INVENTION

The present invention relates to absorbent disposable articles such as sanitary napkins, panty liners, incontinence products and baby diapers. Typically such products comprise the elements of a liquid pervious topsheet, a backsheet and an absorbent core intermediate said topsheet and said backsheet. According to the present invention the topsheet, backsheet and core may be selected from any of the known types of these components provided that they meet certain comfort and protection performance requirements detailed herein. In particular, the key performance criteria have been identified as; the topsheet liquid retention performance which gives an indication of the ability of the topsheet to maintain a dry surface and thereby keep the skin of the wearer dry; the permeability of the absorbent core and its thickness which relate to the absorbent capacity of the core and it ability to allow the flow of vapour and/or air through it and the backsheet wet through/liquid permeability which indicates the ability of the breathable backsheet to retain the absorbed fluid. Furthermore, the individual elements are joined, preferably utilising optimised joining techniques such that the final product also meets specific comfort and performance level criteria also described herein. In addition the absorbent article further comprises an odour control system which in combination with the specific absorbent article element selection provided an improved odour control performance.

Absorbent Article Components

The Topsheet

According to the present invention the absorbent article comprises as an essential component a topsheet. The topsheets suitable for use herein may be any topsheet known in the art.

The topsheets for use herein may comprise a single layer or a multiplicity of layers. In a preferred embodiment the topsheet comprises a first layer which provides the user facing surface of the topsheet and a second layer between the first layer and the absorbent structure/core. The topsheet typically extends across the whole of the absorbent structure and can extend into and form part of or all of the preferred sideflaps, side wrapping elements or wings.

The topsheet as a whole and hence each layer individually needs to be compliant, soft feeling, and non-irritating to the wearer's skin. It also can have elastic characteristics allowing it to be stretched in one or two directions. As used herein the topsheet hence refers to any layer or combination of layers whose principle function is the acquisition and transport of fluid from the wearer towards the absorbent core.

According to the present invention the topsheet may be formed from any of the materials available for this purpose and known in the art, such as non wovens fabrics, films or combinations of both. In a preferred embodiment of the present invention at least one of the layers of the topsheet comprises a liquid permeable apertured polymeric film. Preferably, the upper layer is provided by a film material having apertures which are provided to facilitate liquid transport from the wearer facing surface towards the absorbent structure, as detailed for example in U.S. Pat. Nos. 3,929,135, 4,151,240, 4,319,868, 4,324,426, 4,343,314 and 4,591,523.

According to the present invention the topsheets suitable for use herein must have a topsheet liquid retention of less than 0.22 g, preferably less than 0.15 g, more preferably less than 0.1 g, most preferably 0 g, as defined in the liquid retention test disclosed herein after.

Backsheet

The absorbent article according to the present invention also comprises a breathable backsheet. The backsheet primarily prevents the extrudes absorbed and contained in the absorbent structure from wetting articles that contact the absorbent product such as underpants, pants, pyjamas and undergarments thereby acting as a barrier to fluid transport. In addition however, the breathable backsheet of the present invention permits the transfer of at least vapour, preferably both vapour and air through it and thus allows the circulation of gases into and out of the backsheet. The backsheet typically extends across the whole of the absorbent structure and can extend into and form part of or all sideflaps, side wrapping elements or wings.

According to the present invention any known breathable backsheet or multiple layer breathable backsheet composite may be used in the absorbent article provided that the backsheet meets the requirement of the liquid permeability test as defined herein. The breathable backsheets of the present invention have a liquid permeability at a 7 ml load of less than 0.3 g, preferably of less than 0.2 g, more preferably less than 0.1 g most preferably 0 g.

According to the present invention suitable breathable backsheets for use herein comprise at least one gas permeable layer. Suitable gas permeable layers include 2 dimensional, planar micro and macro-porous films, macroscopically expanded films, formed apertured films and monolithic films. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable 2 dimensional planar layers of the backsheet may be made of any material known in the art, but are preferably manufactured from commonly available polymeric materials. Suitable materials are for example GORE-TEX™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured preformed films are uni directional such that they have at least substantially, if not complete one directional fluid transport towards the core.

Suitable macroscopically expanded films for use herein include films as described in for example in U.S. Pat. Nos. 4,637,819 and 4,591,523.

Suitable monolithic films include Hytrel_, available from DuPont Corporation, USA, and other such materials as described in Index 93 Congress, Session 7A "Adding value to Nonwovens", J-C. Cardinal and Y. Trouilhet, DuPont de Nemours international S. A, Switzerland.

Preferred breathable backsheets for use herein are those having a high vapour exchange, most preferably both a high vapour and high air exchange.

Absorbent Core

According to the present invention the absorbent cores suitable for use in herein may be selected from any of the absorbent cores or core system known in the art provided that certain requirements as concerns caliper and vapour and/or air permeability as defined herein are meet. As used herein the term absorbent core refers to any material or multiple material layers whose primary function is to absorb, store and distribute fluid. The absorbent core of the present invention has a vapour permeability of greater than 500 $g/m^2/s$, preferably greater than 800 $g/m^2/24$ hrs., more preferably 1200 $g/m^2/24$ hrs., most preferably greater than 1500 $g/m^2/24$ hrs. In a preferred embodiment of the present invention the absorbent core also has an air permeability of greater than 200 $l/m^2/s$, more preferably greater than 800 $l/m^2/s$, most preferably greater than 1200 $l/m^2/s$. The absorbent core thus has a caliper of less than 12 mm, preferably less than 8 mm, more preferably less than 5 mm, most preferably from 5 mm to 1.0 mm.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

a Primary/Secondary Fluid Distribution Layer

One optional component of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", "hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orion), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Absorbent Article

The potential benefits of incorporating a breathable backsheet into an absorbent structure have been extensively referred to in prior art but, a simple observation of available products in the market paces clearly points to a basic failure to realise a benefit in use. In many instances the problem has resulted from an inability to control through breathable backsheet wet-through. According to the present invention the absorbent elements meeting the requirements as described herein above must as an essential requirement be combined such that the resultant absorbent article product meets certain performance and comfort indexes herein referred to as the sensory index and the dryness index. The dryness index is a function of the effective breathability test and rewet test of the absorbent article and the sensory index is a function of the effective breathability test, flexibility and caliper of the absorbent article. The test methods are defined herein after. The indices are defined by the equations below:

Dryness index=Effective breathability/(Rewet test)

Sensory index=Effective breathability/(Flexibility*Caliper)

Dryness Index

The Dryness Index is a reflection of one of the unexpected interactions that an absorbent article, particularly a sanitary napkin needs to satisfy, in order to provide overall dryness and/or comfort benefits to the wearer of the product. The dryness index reflects that perceived wetness in use is determined by both the dryness of the wearer facing surface of the product that lies closest to the body in use (i.e. absorbent article rewet test) and the dryness that can be achieved via water vapour exchange with the environment and air circulation via the backsheet (i.e. effective breathability).

Effective Breathability

The effective breathability is determined from the equation below:

Effective Breathability=Vapour Permeability+0.25×Air Permeability

The effective breathability determines a numerical value for the breathability. It considers the two key mechanisms that are likely to participate in exchange of humidity and temperature while wearing a absorbent article having a breathable backsheet. The first mechanism is water vapour exchange via the process of diffusion. This is a continuous process and the mechanism is well understood and represented by a simple diffusion equation. In addition, body motion can result in a change in the relative position of the wearers body and the absorbent article, for example between a sanitary article and the body known as gapping. This motion also is accompanied by a process of air exchange. Repetitive bodily motion can quite literally pump air into and out of the backsheet or at the sides of the product, where a product may not maintain intimate contact to the body. Naturally the stiffer an absorbent article is in the genital region the less likely is this process of pumping to deliver an additional benefit to simple vapour exchange since the product is less deformable and is likely to press up closer to the body like a gasket.

The dryness index provides an indication of the ability of the article to absorb fluids and thus provide protection to the consumer which is given as a function of the permeability of the article and the overall product dryness.

Sensory Index

The Sensory Index is an index that quantifies the relationship between product attributes that need to be satisfied in addition to breathability to deliver a true benefit in use. This is due the cross interactions between unexpected product design elements; namely breathability, the product caliper and product stiffness/flexibility.

Thus in short, the sensory index values gives an indication of the range of values of the permeability, flexibility and caliper of the product according to the present invention which provides protection and comfort benefits.

According to the present invention the absorbent article has a sensory index of greater than 50, preferably greater than 100, more preferably greater than 200, most preferably greater than 300. The article further has a dryness index of greater than 0.5, preferably greater than 2.0, more preferably greater than 4, most preferably greater than 10.

Odour Control System

According to the present invention the breathable absorbent articles comprise as an essential feature an odour control system. It has been found that this combination of a breathable absorbent article with an odour control system results in an unexpected increase in the effectiveness of the odour control system.

Any odour control agent or combinations thereof, known in the art for this purpose may be used herein. The art is replete with descriptions of various odour controlling agents for use in absorbent articles in order to address the problem of malodour formation which may all be usefully employed in the present invention. These agents can typically be classified according to the type of odour the agent is intended to combat. Odours may be chemically classified as being acidic, basic or neutral. Acidic odour controlling agents have a pH greater than 7 and typically include sodium carbonates, sodium bicarbonates, sodium phosphates, particularly zinc and copper sulphates. Basic odour controlling agents have a pH of less than 7 and include compounds such as carboxylic acids such as citric acid, laric acid, boric acid, adipic acid and maleic acid.

Neutral odour controlling agents have a pH of approximately 7. Examples of these types of compounds include activated carbons, clays, zeolites, silicas, absorbent gelling materials, (AGM) and starches. Neutral odour control agents and systems are disclosed for example in EPO 348 978, EPO 510 619, WO 91/12029, WO 91/11977, WO 91/12030, WO 81/01643 and WO96/06589. Also cyclodextrin and derivatives thereof may be used as described in U.S. Pat. No. 5,429,628.

Alternatively, the odour control systems may be categorised with respect to the mechanism by which the malodor detection is reduced or prevented. The above odour control agents typically control odour detection by an absorptive mechanism.

Hence, odour control systems which chemically react with malodourous compounds or with compounds which produce malodourous degradation products thereby generating compounds lacking odour or having an odour acceptable to consumers may also be utilised herein. Suitable agents include chelating agents and may be selected from amino carboxylates such as for example ethylenediaminetetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odour control system for use herein comprises a buffer system, such as citric acid and sodium bicarbonate, sodium phosphate and sorbic acid buffer systems. Also, buffer systems having a pH of from 7 to 10 as described for example in WO94/25077 may be useful herein.

An alternative odour control system utilises ion exchange resins such as those described in U.S. Pat. Nos. 4,289,513 and 3,340,875.

Masking agents such as perfumes may also be used as odour control agents herein. Preferably these agents are used in combination with an additional odour control agent such as zeolite as described in WO94/22500.

Preferred odour control systems for use herein include the following combinations i). silica, AGM and zeolites, preferably in a ratio of from 5:1:1 to 1:1:5 most preferably 3:1:1 to 1:1:3 ii) zeolites, activated carbon and AGM, iii) silica and AGM preferably in a ratio of from 5:1 to 1:5, more preferably from 3:1 to 1:3 iv) zeolites and AGM, v) silica and zeolites, preferably in a ratio of from 1:5 to 5:1, more preferably from 1:3 to 3:1 vi). chelating agents, particularly ethylenediamine- tetracetate, and vii). chelating agents in combination with an odour control absorber system i) or ii) preferably at a ratio of from 1:10 to 10:1, more preferably from 1:5 to 5:1

According to the present invention the amount of odour control system incorporated into the absorbent article may be readily determined by the man skilled in the art and is to some extend dependent on the end use of the absorbent article and bearing in mind the absorbent article dimensions. Typically the absorbent article comprises from 5 $gm^{-2}$ to 400 $gm^{-2}$, more preferably from 100 $gm^{-2}$ to 300 $gm^{-2}$, most preferably from 150 $gm^{-2}$ to 250 $gm^{-2}$ basis weight of said odour control system. For example a sanitary napkin or panty liner may comprise from 0.25 g to 5 g, preferably from 0.4 g to 3 g, most preferably from 0.5 g to 2.5 g of said odour control system.

The odour control system may be incorporated into the article by any of the methods disclosed in the art, provided that the absorbent article elements and the absorbent article itself meets the specified requirement described herein. For example, the odour control agents may be layered on the core of the absorbent material or mixed within the fibres of the absorbent core. The odour control system is preferably incorporated between two layers of cellulose tissue. Optionally the odour control system may be bonded between two cellulose tissue layers with for example a hot melt adhesive or any suitable bonding system.

Absorbent Article Construction

A further aspect of the present invention relates to the joining of the topsheet, backsheet and absorbent core elements to provide the absorbent article. According to the present invention at least two, preferably all of the elements of the article are joined.

Each of said elements comprising at least one layer has a wearer facing surface and a garment facing surface. Typically, adjacent garment facing surfaces form a common interface with the wearer facing surface of an adjacent element or layer. The elements or layers are joined together across this common interface. In this manner the topsheet is joined to the absorbent core, and the core is joined to the backsheet. Furthermore, each of said topsheet, backsheet and core elements may comprise more than one layer and these layers may also be similarly joined. In addition the topsheet may be directly or indirectly by joined to the backsheet at the periphery of the absorbent article.

The elements and layers thereof may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. crimping), embossing, and/or pressure bonds, or dynamic mechanical bonds. According to an embodiment of the present invention the preferred means of joining is adhesive. Suitable adhesives include non pressure sensitive and cold adhesives. The adhesive may be applied by any means known in the art such as spiral application, slot coating, spraying, spiral spraying, curtain coating, control coating and printing, provided that the adhesive does not substantially affect the breathability.

In a preferred embodiment of the present invention the inter element or inter layer joining adhesive is selected and applied so as to reduce any impact it may have on the effective breathability of the absorbent article and preferably also the flexibility of the absorbent article, In this manner the dryness index and sensory index values may in fact be increased. Since many commonly utilised adhesives are not vapour permeable it is highly preferable to minimise the amount of adhesive used to join the layers/elements of the absorbent article in order to minimise their impact on the permeability (breathability) and preferably also the flexibility of the absorbent article. One means of achieving this is to use particular adhesive application methods such as open adhesive application techniques, whereby areas of the common interface are adhesive free, whilst retaining the required level of attachment/joining of the two adjacent layers or elements. In particular spiral spraying is preferred. The layers and elements should be joined in such a manner so that the absorbent article product maintains structural integrity but no more. This method finds particular application for the interlayer joining of the backsheet element layers and the joining of the backsheet element and the absorbent core element. Alternatively adhesives which are vapour permeable may be used.

Preferably not more than 40%, more preferably less than 20%, most preferably less than 10% of the common interface of two adjacent layers or elements is joined. Furthermore, the density of the adhesive should be reduced and a thin application of adhesive is preferred.

In a preferred embodiment of the present invention wherein the absorbent article finds utility as a sanitary napkin or panty liner, the absorbent article is also provided with a panty fastening means which provides means to attach the article to an undergarment. For example the panty fastening means may comprise a mechanical fastener such as hook and loop fasteners such as marketed under the tradename VELCRO, snaps or holders. Alternatively, the article is fastened to the undergarment by means of panty fastening adhesive on the backsheet. The panty fastening adhesive provides a means for securing the article to the panty and preferably a means for securing the article when soiled, to the fold and wrap package for convenient disposal. Typically, at least a portion of the garment facing surface of the backsheet is coated with adhesive to form the panty fastening adhesive. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J., 3 Sigma 3153 manufactured by 3 Sigma and Fuller H-2238ZP manufactured by the H.B. Fuller Co.

The panty fastening adhesive is typically applied to the backsheet by slot coating. In order to reduce the effect of the breathability of the backsheet and thus of the article as a whole, the adhesive is preferably applied such that at least 60%, preferably from at least 80%, most preferably at least 90% of the surface of the backsheet is adhesive free. The required adhesiveness can still be achieved even when using reduced surface coverage by using a particular distribution such as thinner strips, discontinuous strips of adhesive, intermittent dots, random patterns spirals.

The panty fastening adhesive is typically covered with a removable release paper or film in order to prevent the adhesive from drying out or adhering to another surface other than the panty prior to use. Any commercially available release paper or film may be used. Suitable examples include BL 30MG-A SILOX EI/O and BL 30 MG-A SILOX 4 P/O available from Akrosil Corporation.

According to the present invention the absorbent article can be used beneficially in the context of sanitary napkins, panty liners, incontinence articles and diapers. However, sanitary napkins and panty liners are particularly susceptible to the present invention. The absorbent article may thus also have all those features and parts which are typical for products in the context of their intended use such as elastic fastening devices and wings.

TEST METHODS

Absorbent Article Component Tests

Topsheet Retention Test

The topsheet retention test is utilised to assess the liquid retention character (of bodily discharges) of topsheet materials or composites that may be used on disposable absorbent articles and particularly sanitary napkins.
Basic Principle of the Methods The basic principal of the test is to evaluate the liquid retention behaviour of alternative topsheet materials to liquids that simulate bodily discharges. A "good topsheet material" in this test can be a film (e.g. apertured formed film) or a fibrous or a fibrous nature film provided it has a low propensity to acquiring and retaining liquids either on or within its structure. Naturally a "good topsheet" is also, in addition to having low retention properties expected to allow rapid transmission of bodily discharges further into the article and to hinder discharges that are contained within the article from returning to the upper (body side) surface of the article. Additionally a "good topsheet" should also maintains a clean appearance during use of the articles.

To assess the topsheets retention to liquid, a test is performed as detailed below:

Two sheets (with dimensions of 5 cm×5 cm) of a commercially available airlayed absorbent tissue each with a basis weight of 63 g/m$^2$ available from Walkisoft USA under the supplier code Metmar (P50W.IPED) are utilised to simulate an absorbent core.

A sample of the topsheet material (with dimensions of 5 cm×5 cm) that is to be assessed is placed directly on top of this absorbent structure. A standardised test liquid closely matching menses in viscosity and electrical conductivity (see below) is dripped onto the centre of the test sample from a height of 3 cm and at a rate of 2 g/min. until a total of 2 grams has been introduced onto the sample. The sample is left without further interference for a period of 1 minute.

Following the 1 min. waiting period a transparent block (1 cm thick with dimensions 8.5 cm×8.5 cm) is placed on top of the test sample and a weight is lower gently onto the total assemble for a period of 5 minutes. The total pressure exerted onto the test sample, at this point, is 70 g/cm$^2$.

The weight and transparent block is removed and carefully the topsheet sample is removed and placed on a stack of 2 sheets (with dimensions 12 cm×12 cm) of commercially available filter/blotting paper {produced by Cartiera Favini S.p.A. Italy; Type Abssorbente Bianca "N30" (local vendor Ditta Bragiola SpA. Perugia, Italy)} that have been pre-weighed. A second stack of 2 pre-weighed filter papers are placed on top of the topsheet sample. A second weight is placed on top of the filter paper stack containing the topsheet sample. The second weight exerts a pressure onto the filter paper stack of 130 g/cm$^2$ for a period of 15 seconds. The weight (for this critical step) is attached to a hydraulic arm. The lowering of the weight and time the sample is placed under pressure is controlled via a simple electronic device to ensure reproduceability from one test to the next.

The second weight is removed and each (lying above and below the topsheet sample) filter paper stack is weighed and the difference for each surface (liquid pick-up from the topsheet sample) recorded. Materials that have a zero pick-up value for the top surface (placed normally in contact with the users skin) are given a zero "topsheet retention" value independent of having a non-zero value for the bottom surface as these materials clearly demonstrate non-communication between the upper and lower surfaces.

Test Solution: Preparation of Test Solution Paper Industry Fluid (PIF)

The test solution PIF is a widely used test liquid in the Paper industry due to its simple composition, ability to prepare and maintain high standards of solution quality and its similarity to human menses with respect to viscosity and ionic surface tension.

The solution PIF is prepared by dissolving the following reagent components, at the indicated quantities, into 1 liter of distilled water. Care should be taken in dissolving the solid components and particularly the Carboxylmethylcellulose. Typically the solid components should be added over a period of one hour slowly and with constant stirring of the solution (via a magnetic stirring device).

Supplier Sigma Chemicals, USA

| Chemical Component - | Usage/1L |
|---|---|
| 1) Carboxymethylcellulose, Sodium salt low viscosity: Order No. = C 5678, | 15 grams |
| 2) Sodium bi-Carbonate, Crystalline: Order No. = S 8875 | 4 grams |
| 3) Sodium Chloride (AR): Order No. = S 9625 | 10 grams |
| 4) Glycerol (>99% pure): Order No. = G 5516 | 80 grams |

REPRESENTATIVE TOPSHEET EXAMPLES

Representative topsheet samples commonly used in hygienic articles and available from a range of companies have been tested and the results are detailed in the attached Table.

| Material Sample Type (supplier and material code) | Topsheet Retention (g) |
|---|---|
| Example 1: CPM | Top Surface = 0.00 |
| Supplier Code: X-1522 | Bottom Surface = 0.09 |
| Tredegar Film Products B.V. Holland | Topsheet Retention = 0.00 * |
| Example 2: Film/Nonwoven Composite** Film Supplier Code: BPC 5105 CPM | Top Surface = 0.00 |
| BP Chemical Germany | Bottom Surface = 0.15 |
| Nonwoven Supplier Code: ARBO TB/_BI | Topsheet Retention = 0.00 * |

-continued

| Material Sample Type (supplier and material code) | Topsheet Retention (g) |
| --- | --- |
| Mequinenza Spain | |
| Example 3: CPT (LDPE) | Top Surface = 0.00 |
| Supplier Code: 15112 | Bottom Surface = 0.09 |
| Tredegar Film Products B.V. Holland | Topsheet Retention = 0.00 * |
| Example 4: Hydrophilic Thermally Bonded Nonwoven | Top surface = 0.10 |
| Supplier Code: NW/ThBo/Hy | Bottom Surface = 0.16 |
| Pantex s.r.l (Italy) | Topsheet Retention = 0.26 |
| Example 5: Pantex Hydrophobic | Top Surface = 0.09 |
| Supplier Code: Pantex (PT2) | Bottom Surface = 0.11 |
| Pantex s.r.l (Italy) | Topsheet Retention = 0.20 |
| Example 6: Amoco Nonwoven | Top Surface = 0.09 |
| Supplier Code: Amoco P8 | Bottom Surface = 0.09 |
| Amoco GmbH, Germany | Topsheet Retention = 0.18 |

**as found on current Alldays Duo Active panty liners manufactured by P & G Germany)
*3-D apertured films do not allow moisture on the bottom surface to migrate to the top surface as evidenced by the top surface value hence zero is recorded for the value of moisture in contact with the skin.

Vapour and Air Permeability Test: Absorbent Core

The air permeability test is utilised to assess the ability of the absorbent core to exchange/circulate vapour and preferably air and is carried out on the core material as detailed for an absorbent article.

Representative Absorbent Core Examples

The air/vapour permeability of representative examples of absorbent core elements has been assessed. The absorbent core have been manufactured under normal manufacturing procedures by P & G Pescara Technical Centre (Italy) or removed from available market products.

Example 1

The core material is a tissue laminate (20 cm×6.5 cm) composed of a folded stack 2 layers of airlayed tissue of 63 g/m² basis weight {available from Walkisoft Finland under the supplier code Metmar (P50W.IPED)}. Between the two tissue layers the laminate contains AGM (available from Shokubai Japan under the supplier code; Aqualic L-74 Optimised) at a basis weight of 50 g/m² and has a caliper of 2.2 mm.

Example 2

The core material is a tissue laminate (15 cm×4.0 cm) composed of a 2 layers of airlayed tissue of 55 g/m² basis weight {available from Unikay Italy under the supplier code Unikay 303 LF}. Between the two tissue layers the laminate contains AGM (available from DOW Chemicals Germany under the supplier code; DOW 95890.1) at a basis weight of 79 g/m², and a zeolite (available from Degussa Germany under the supplier code; Wessalith CS) at a basis weight of 105 g/m2. The core has a caliper of 1.4 mm. The core laminate was manufactured and supplied by Korma Italy (under the manufacturing code: KO 040 02 003).

Example 3

The core material is a tissue laminate (20 cm×6.5 cm) composed of a 2 layers of airlayed tissue of 55 g/m² basis weight {available from Unikay Italy under the supplier code Unikay 303 LF}. Between the two tissue layers the laminate contains AGM (available from DOW Chemicals Germany under the supplier code; DOW 95890.1) at a basis weight of 67 g/m², a zeolite (available from Degussa Germany under the supplier code; Wessalith CS) at a basis weight of 50 g/m² and activated charcoal (available from Chemviron Belgium under the supplier code; Chemviron SCII) at a basis weight of 40 g/m² The core has a caliper of 1.6 mm. The core laminate was manufactured and supplied by Korma Italy (under the manufacturing code: KO 065 01 003).

| Examples | Caliper mm | Vapour Permeability $g/m^2$/24 hrs. | Air Permeability $l/m^2/s$ |
| --- | --- | --- | --- |
| Example 1: | 2.2 | 2034 | 4000 |
| Example 2: | 1.4 | 1990 | 2440 |
| Example 3: | 1.6 | 2010 | 2290 |

Liquid Permeability Test: Backsheet

The liquid permeability test is utilised to quantify the barrier properties of breathable backsheet materials or constructions that could be utilised on a breathable absorbent article and particularly on a sanitary napkin or a panty liner.

Basic Principle of the Methods

The basic principle of the test is to evaluate the performance of backsheet materials or constructions to liquids which simulate bodily discharges. A "good backsheet layer or construction" is expected to be sufficiently open to be classified as breathable but, without being too open to the passage of bodily discharges. To ensure that this test is sufficiently representative to the situation when the absorbent article in particular sanitary napkins is actually used a test solution closely resembling human menses is utilised, referred to herein as Artificial Menstrual Fluid (AMF). AMF is based on modified sheeps' blood as detailed in the solution preparation method detailed below.

To determine the liquid permeability of a backsheet or backsheet construction, a standard absorbent structure with the backsheet material or construction is prepared and placed flat on a transparent test stand made of transparent. The sample to be tested is oriented with the absorbent structure exposed (upper side) and the breathable backsheet side in contact with the transparent test stand (lower side). Suspended above the sample to be analysed is a liquid delivery system that is capable of delivering any desired quantity of the test liquid.

The standard absorbent structure is composed of 4 layers (folded as a stack) of airlayed tissue of 63 g/m² basis weight {available from Walkisoft USA under the supplier code Metmar (P50W.IPED)} having dimensions of 20 cm×6.5 cm. The backsheet is then placed on top of this structure without any additional adhesive attachment.

Located between the back most surface (garment facing surface) of the test sample and the transparent test stand are two sheets of absorbent filter paper {produced by Cartiera Favini S.p.A. Italy; Type Abssorbente Bianca "N30" (local vendor Ditta Bragiola SpA. Perugia, Italy)}. The absorbent filter paper is in intimate contact with the backsheet of the test sample to simulate, for example a sanitary napkin attached to a panty or a diaper/incontinence device in close contact with the clothing. Directly below the transparent test stand is a mirror so positioned to allow any red colour change in the absorbent filter paper to be continuously observed. For example, if the backsheet is unable to adequately resist liquid transmission then the filter paper will become wet with the red AMF solution and this can be observed in the mirror. The magnitude of the transmitted solution is determined by simply weighing the absorbent filter paper.

The test solution is introduced to the test sample via a calibrated delivery system such as via a simple burette according to the desired test approach as detailed below. Once loaded the test sample is then placed under a pressure of 70 g/cm$^2$ which is believed to reflect more stressful pressures that are nevertheless regularly obtained in-use. The test sample remains under the 70 g/m$^2$ pressure for a period of up to 5 mins. At which time the weight is removed and the absorbent filter paper is weighted to determine if and to quantify the extent of liquid that has been transported through the backsheet or backsheet construction.

The process is then repeated entirely with an additional introduction of liquid to the test sample. For each introduction of liquid a new stack of absorbent filter papers (pre-weighed) is used to be able to better determine the liquid barrier behaviour as a function of load.

The Loading Steps are Specifically:
Step 1 5 ml
Step 2 1 ml
Step 3 1 ml

A good backsheet layer or layered construction is expected to have a liquid permeability of less than 0.3 g for the above conditions. Preferred backsheet should also have a liquid permeability of less than 0.3 g for step wise increased loads of 1 ml until a total load of 9 ml., preferably 11 ml. more preferably 13 ml. and most preferably 15 ml. load has been reached.

Preparation of Test Liquid AMF

Artificial Menstrual Fluid (AMF) is based on modified sheep's blood that has been modified to ensure it closely resembles human menstrual fluid in viscosity, electrical conductivity, surface tension and appearance. In addition we introduce a surfactant (1%) to this test fluid (supplied by Pegesis/USA) to better reflect stress situations in which typical hygiene practice (and in some limited situations, dietary influences) may introduce additional surfactants or unexpected levels of, for example, fatty acids, that might lower the blood surface tension. Low surface tension menses is the biggest contributor to through backsheet wet-through failure on a breathable absorbent article such as a sanitary article.

Reagents
1) Difibrinated sheep's blood is available from Unipath S.p.A {Garbagnate Milanese/Italy}.
2) Lactic Acid from J. T. Baker Holland Reagent Grade (85–95% w/w)
3) Potassium Hydroxide (KOH) from Sigma Chemical Co. USA, Reagent grade
4) Phosphate Buffer Saline Tablets from Sigma Chemical Co. USA, Reagent grade
5) Sodium Chloride from Sigma Chemical Co. USA, Reagent grade
6) Gastric Mucine from Sigma Chemical Co. USA, Type III (CAS 84082-64-4)
7) Distilled Water.

Step 1
Prepare a 9±1% Lactic Acid Solution by dissolution of lactic acid powder and distilled water.
Step 2
Prepare a 10% Potassium Hydroxide (KOH) solution by dissolving KOH powder into distilled water.
Step 3
Prepare a Phosphate buffer solution buffered to pH=7.2. by dissolving tablets as directed into 1 L distilled water.
Step 4
Prepare and slowly heat to 45±5° C. a solution of the following composition:
460±5 ml of phosphate buffer solution
7.5±0.5 ml of KOH solution
Step 5
Prepare a Mucous Solution by slowly dissolution (with constant stirring) of approximately 30 grams of gastric mucine in the pre-heated (45±5° C.) solution prepared in step 4. Once dissolved the solution temperature should be increased to between 50–80° C. and the mixture covered for approximately 15 mins. Turn the heat down to maintain a relatively constant temperature between 40 and 50° C. and continue to stir for a period of 2.5 hrs.
Step 6
Remove the solution from the hot plate and allow the solution (from step 5) to now cool to less than 40° C. Add 2.0 ml of the 10% lactic acid solution and mix thoroughly for 2 mins.
Step 7
Place the solution in an Autoclave and heat to a temperature of 121° C. for 15 mins.
Step 8
Allow the solution to cool to room temperature and dilute 1 to 1 with the di-fibrinated sheep's blood.

Following AMF preparation its viscosity, pH and conductivity are measured to ensure the blood characteristics lie in a range close to that of normal menstrual blood {(see reference H. J. Bussing "zur Biochemie des Menstrualblutes" Zbl Gynaec, 179,456 (1957)}. The viscosity should lie in the range of 7 to 8 (units cStK). The pH should lie in the range of 6.9 to 7.5 and the conductivity in the range 10.5 to 13 (units mmho). If the viscosity is not within the range specified above it should not be used and a new batch of AMF needs to be prepared. This may require adjustment to the quantity of gastric mucine used. Since this is a natural product its composition may alter from one lot to another.

For individual measurements typically 100 ml AMF test solution with surfactant is prepared by mixing 90 ml AMF solution (maintained at 25° C.) with 10 ml Surfactant. The AMF/1% surfactant solution must be constantly mixed to ensure the components do not separate prior to usage. The solution should be used only within 4 hours of preparation.

BACKSHEET EXAMPLES

Example 1

In this example a backsheet currently incorporated in Always Ultra (normal size) available from Procter & Gamble Pescara Technical Centre was tested. The backsheet supplied by Clopay USA (under supplier code DH215 peach) is not a breathable backsheet.

Example 2

The backsheet is a multi-layer construction composed of two layers. The first layer that is placed directly in contact with the absorbent tissue layer is a formed apertured film (CPT) made of Low Density PE {supplied by Tredegar Film Products B. V. Holland under the manufacturing code X-1522}. The bottom most layer that would lie, in-use, directly in contact with the wearers panty is composed of a nonwoven laminate {14MB/14 SB manufactured by Corovin GmbH in Germany under the trade name MD 2005}. The nonwoven laminate is composed of 14 g/m$^2$ spunbond and 14 g/m$^2$ meltblown.

Example 3

The backsheet is comprised of two layers. The first layer is a formed apertured film made of a blend of low and high density PE with a crush resistant hexagonal hole configuration {supplied by Tredegar Film Products B.V. Holland under the manufacturing code AS 225 MD 25}. The second layer is an improved nonwoven laminate composed of 3 layers with basis weights 14 g/m² spunbond—20 g/m² meltblown—14 g/m² spunbond (manufactured by Corovin GmbH in Germany under the trade name MD 3005).

Example 4

This is also an example of a 2 layer backsheet construction. The first layer that is placed directly in contact with the absorbent tissue layer is a formed apertured film made of a blend of low and high density PE with a crush resistant hexagonal hole configuration {supplied by Tredegar Film Products B.V. Holland under the manufacturing code AS 225 MD 25}. The second garment facing layer is composed of a simple microporous film {supplied by Exxon Chemical Company under the manufacturing code Exxaire XBF-102W}.

Example 5

In this example a single backsheet layer is utilised. The layer is a laminated nonwoven structure composed of a Polyethylene nonwoven (supplied by Corovin Germany under the code HDPE #17870) onto which a uniform layer (0.8 mil/~20 g/m²) of DuPont Hytrel (supplied by DuPont Corporation, USA) polyester-based film has been co-extruded. (this material was manufactured at request of P & G Cin./USA by Clopay USA under the trial code P18-3097/0.8).

|  | Liquid Permeability (g) | | | | |
| --- | --- | --- | --- | --- | --- |
| Example | 7 ml | 9 ml | 11 ml | 13 ml | 15 ml |
| Example 1 | zero | zero | zero | zero | zero |
| Example 2 | zero | zero | 0.2 | 0.4 | 0.55 |
| Example 3 | zero | zero | zero | zero | zero |
| Example 4 | zero | zero | zero | zero | ~zero (commensing) |
| Example 5 | zero | zero | zero | zero | zero |

ABSORBENT ARTICLE TESTS

The following tests were carried out on selected exemplified absorbent articles detailed below:

REPRESENTATIVE EXAMPLES

Representative examples of sanitary napkins or panty liners according to the present invention incorporating a breathable backsheet and manufactured under normal manufacturing procedures by Procter & Gamble Pescara Technical Centre (Italy) SpA and Procter and Gamble GmbH Germany were tested. An additional market product that does not feature a breathable backsheet has been included to provide a comparison of products representative of current technology.

Example 1

In this example currently available Always Ultra (normal size) market product was tested. The product was manufactured according to normal manufacturing procedures by Procter & Gamble Pescara Technical Centre (Italy) SpA. The topsheet corresponds to the topsheet exemplified in example 1 of the topsheet examples and the core corresponds to the core exemplified in example 1 of the core examples. The backsheet on this product is not a breathable backsheet.

Example 2

This is an example of a panty liner, which is based on currently available Alldays Duo Active, manufactured by Procter and Gamble in Germany. In this example the topsheet corresponds to the topsheet exemplified in example 2 of the topsheet examples and the core corresponds to the core exemplified in example 2 of the core examples. However the backsheet consists of a multi-layer breathable backsheet construction as exemplified by example 2 in the backsheet retention test is used. The first backsheet layer that is placed directly in contact with the absorbent core is a formed apertured film (CPT) made of Low Density PE {supplied by Tredegar Film Products B.V. Holland under the manufacturing code X-1522}. The bottom most layer that would lie, in-use, directly in contact with the wearers panty (garment facing layer) is composed of a nonwoven laminate {14MB/14SB manufactured by Corovin GmbH in Germany under the trade name MD 2005}. The nonwoven laminate is composed of 14 g/m² spunbond and 14 g/m² meltblown. Each backsheet layer is joined over the full surface by a extensively overlapped spiral glue application at a basis weight of approximately 8 g/m². The glue utilised for attachment of both backsheet layers was supplied by SAVARE' SpA. Italy (under the material code PM17). The attachment of the product to the panty is provided for by five stripes of adhesive (material code Lunatak HL-2238 X supplied by Fuller GmbH, Germany). The stripes run the full panty liner length (about 150 mm) and each is 5 mm wide.

Example 3

This example is a modified Always Ultra sanitary napkin. The topsheet corresponds to the topsheet exemplified in example 1 of the topsheet examples and the core corresponds to the core exemplified in example 3 of the core examples. A multi-layer breathable backsheet construction as exemplified by example 3 in the backsheet retention test is used. The formed apertured film backsheet layer utilised is a blend of low and high density PE with a crush resistant hexagonal hole configuration {supplied by Tredegar Film Products B.V. Holland under the manufacturing code AS 225 HD 25}. The second backsheet layer is also an improved nonwoven laminate composed of 3 layers with basis weights 14 g/m² spunbond—20 g/m² meltblown—14 g/m² spunbond (manufactured by Corovin GmbH in Germany under the trade name MD 3005). In addition the inter layer/element glue attachment has been optimise to enhance both the flexibility and breathability of the article. The inter-layer gluing design is a low basis weight (6 g/m²) spiral glue pattern (2 spirals each 10 mm wide and 160 mm long separated by 20 mm). This gluing design is used to join the first backsheet layer (apertured film) to the absorbent core. The attachment of the second backsheet layer is via low basis weight spiral glue application only at the perimeter of the product. A glue free window of approximately 40 mm wide and 170 mm long and centered in the product is used to enhance the pad flexibility. The glue utilised for joining of both backsheet layers was supplied by SAVARE' SpA. Italy (under the material code PM17). The attachment of the product to the panty is provided for by two stripes of adhesive (material code Lunatak HL-2238 X supplied by Fuller GmbH, Germany). The stripes are 170 mm long, each is 22 mm wide and a gap of 11 mm exists between the stripes which are centered both length and breadthwise on the article.

Example 4

This example is another example of a modified Always Ultra sanitary napkin. The topsheet corresponds to the topsheet exemplified in example 1 of the topsheet examples and the core corresponds to the core exemplified in example 3 of the core examples. A two layer backsheet construction as exemplified by example 4 in the backsheet retention test is used. The first layer backsheet that is placed directly in contact with the absorbent tissue core is a blend of low and high density PE with a crush resistant hexagonal hole configuration {supplied by Tredegar Film Products B.V. Holland under the manufacturing code AS 225 HD 25}. The second backsheet layer that would lie, in-use, directly in contact with the wearers panty is composed of a microporous film {supplied by Exxon Chemical Company under the manufacturing code Exxaire XBF-102W}. The inter-layer/element gluing design is a low basis weight (6 g/m$^2$) spiral glue pattern (2 spirals each 10 mm wide and 160 mm long separated by 20 mm). This is used to join both the first backsheet layer (apertured film) to the absorbent core and the second microporous film backsheet layer to the first backsheet layer (the apertured film). The second backsheet layer is also joined at the perimeter by a temperature/pressure fusion process (crimp) as utilised in the current Always market product in Europe. The glue utilised for joining both backsheet layers was supplied by SAVARE' SpA. Italy (under the material code PM17). The attachment of the product to the panty is identical to that used in example 3.

Example 5

This example is again a sanitary napkin. The topsheet corresponds to the topsheet exemplified in example 1 of the topsheet examples and the core corresponds to the core exemplified in example 3 of the core examples. The backsheet utilised is exemplified by example 5 in the backsheet retention test and features a single layer laminated nonwoven structure composed of a Polyethylene nonwoven (supplied by Corovin Germany under the code HDPE #17870) onto which a uniform layer (0.8 mil/~20 g/m$^2$) of DuPont Hytrel (supplied by DuPont Corporation, USA) polyester-based film has been co-extruded. (this material was manufactured at request of P & G Cin./USA by Clopay USA under the trial code P18-3097/0.8). The backsheet is joined to the core using a low basis weight (6 g/m) spiral glue pattern ( 2 spirals each 10 mm wide and 160 mm long separated by 20 mm). The attachment of the product to the panty is identical to that used in example 3.

Example 6

In this example a market product has been assessed; The product, Silhouettes Ultra (normal plus size) Manufactured by Johnson & Johnson, Montreal Canada (Print code on bag; 51564 19:23) and imported into Italy by Johnson & Johnson Roma. The product claims an odor control benefit, but it does not contain a breathable backsheet and is thus not representative of the present invention.

Air & Vapour Permeability Test on Absorbent Article Products

The Vapour permeability test is utilised to quantify the vapour transmission properties of breathable absorbent articles.

Basic Principle of the Methods

The basic principle of the test is to quantify the extent of water vapour transmission of an absorbent article. The test method that is applied is based on a standardized textile industry applied test method and commonly referred to as the "cup test method". The test is performed in a stable temperature/humidity laboratory maintained at a temperature of 23° C. at 50% RH for a period of 24 hours.

Apparatus
1) Sample cup of dimensions specified in the drawing (open area=0.00059 m$^2$)
2) Syringe to introduce the distilled water into the completed sample cup.
3) Wax to seal the cup once sample has been arranged.
4) A circular punch to facilitate preparation circular samples of diameter=30 mm.
5) Laboratory of stable climatic conditions (23° C./±0.5° C.±50% RH±1% RH)
6) Laboratory balance accurate to 4 decimal places.

Sample Preparation/Measurements

The test is be performed on the absorbent article product. A representative article is selected and a sample is cut to size using the punch. The sample cut is sufficiently large to adequately overlap the sample holder and to ensure material that may have been damaged or undesirably stretched due to the cutting operation lies outside of the measurement centre when the measurement is performed. The sample is so arranged onto of the sample cup so as to fully overlap the cup. The sample is oriented so as to ensure that the surface exposed to the laboratory environment is the same that would be found while wearing the article.

The closure ring of the sample cup is then placed onto the sample and pushed down. This ensures that the excess material is held firmly in place and does not interfere with the measurement. A wax is then applied to the entire surface of the closure ring to ensure the whole upper part of the apparatus is closed to the environment. Distilled water (5±0.25 ml) is introduced with the syringe into the sealed sample cup via the minute perforation. Finally this perforation is sealed with silicone grease.

The entire cup (containing sample and water) is weighed and the weight recorded to 4 decimal places. The cup is then placed in a ventilation stream generated by a fan. The air flowing over the top of the sample cup is 3±0.3 m/sec and confirmed via a wind velocity meter ("Anemo", supplied by Deuta SpA., Italy). The sample cup remains in the ventilated test field for a period of 24 hrs and is then re-weighted. During this period if the test sample is sufficiently breathable the liquid in the sample holder is able to diffuse out of the sample holder and into the laboratory environment. This results in a reduction in the weight of water in the sample holder that can be quantified on re-weighing the complete sample cup following the 24 hr period.

The vapour permeability value is determined as the weight loss divided by the open area of the sample holder and quoted per day.

i.e. Vapour Permeability=Weight Loss (g)/(0.00059 m$^2$/24 hrs)

Air Permeability Test

The air permeability test is utilised to assess the ability of an absorbent structure to circulation/exchange air.

Basic Principle of the Methods

The basic principle of the test is to evaluate the resistance of an absorbent article to the passage of air. In this test, the volume (or amount) of air that flows through an article of given dimensions under standard conditions (of 23° C./50% RH) is measured. The instrument utilised for the test is: Air Permebilimeter FX 3300 manufactured by TexTest AG Switzerland.

Samples should be allowed to equilibrate in the test environment for at least 4 hrs prior to commencement of the measurement. The article (having dimensions exceeding 5 cm² the dimensions of the measurement head) is placed on the device as instructed by the manufacturer. An aspiration pump set to generate a pressure of 1210 kPa that sucks air through the sample layer or structure. The device measures the volume of air flow and the pressure drop across the orifices that contains the sample and measurement head. Finally the device generates a value of air permeability in the units of "I/m²/s".

In the case of vapour and air permeability measurements on a finished product the area of Panty Fastening Adhesive (PFA) can influence the results particularly if the adhesive is applied as is typically the case as an impervious stripe of adhesive via a slot coater. The measurements of both air and vapour permeability need to be representative of the total product. One simple way to ensure a representative measurement is to assess backsheet samples with some PFA coverage. For example in the case of Example 3, 4 and 5 the total backsheet area is covered to a degree of 45% with PFA. The vapour and air permeability measurements are thus performed on the samples featuring a 45% surface coverage by PFA adhesive.

Rewet Test

Basic Principle of the Methods

In this context the rewet method is utilised to assess the dryness of the product with respect to the wearer facing surface of the product . In combination with additional test methods that assess the dryness of the product with respect to the openness of the backsheet (air & vapour permeability test) it allows the total product dryness to be represented.

The test solution that is utilised for this test is based on the Paper Industry Fluid (PIF) that has been extensively utilised (due to its stability and high reproducibility) and due to its close similarity to human menses in terms of viscosity and liquid surface tension & ionic strength. The solution preparation is detailed below.

Apparatus

1) Blotting Paper available from Schleicher & Schuell (Germany). S & S Rundfilter/Durchmesser 150 mm, No. 597, Reference-No.: 311812.
2) A weight of 4200 g covered on the lower surface with a foam of moderate flexibility. Both the weight and foam are covered with a thin, flexible plastic film to maintain waterproofs. The weight dimensions should allow a 6 cm×10 cm surface to contact the article under examination. Pressure exerted onto the article=70 g/cm².
3) A perspex (7 mm thick) plate of dimensions 6 cm×10 cm with a hole of dimensions 3 cm×4 cm centred in the template.
4) A burette capable of introducing the test fluid at a reproducible rate of 7 ml in 90 seconds.
5) An analytical balance capable of reading to 4 decimal places.

Sample Preparation/Measurement

The article to be assessed is removed from any packaging and placed on a flat laboratory surface and centred directly below the burette for test liquid delivery. The transparent plate is placed on the surface and the PIF test liquid is introduced over the exposed area corresponding to the hole in the transparent plate. After 90 seconds 3.5 ml of PIF have been introduced to the sample and an electronic counter set to 20 mins. is activated. During this waiting period a stack of 7 discs of filter paper are weighed on the analytical balance and noted.

After 20 mins. the transparent plate is removed and the stack of filter papers are positioned centrally on the article being assessed and the weight is gently lowered onto the filter paper stack. The article and filter paper stack remain under the pressure exerted by the weight for a period of 15 seconds, after which the weight is carefully removed and the filter paper stack is re-weighted. The difference in weight (to the nearest milligram) is recorded as the rewet value. The tests are repeated for at least 10 samples to ensure adequate accuracy of the measurements.

Flexibility Test & Caliper Test

Basic Principle of the Methods

The flexibility test is utilised to quantify the product flexibility or product stiffness in the cross direction. Most flexibility tests have attempted to establish a product benefit based on a product design change using a range of flexibility test methods to quantify this such as measuring the drape (bend ability) of a product or the combination of stiffness in both length and cross direction. The flexibility test used herein is a dynamic stiffness measurement (force to deform vs. distance deformed) which determines the resistance of a product to deform in the cross direction. The higher the stiffness value the more the product is likely to push against the sensitive skin of the wearers inner thighs and create a sensory negative during various bodily motions.

Apparatus

1) Climatically controlled Lab

Maintenance of 23° C. and 50% Relative humidity.

2) Instron Limited, UK Model 6021

Interfaced to a standard IBM with RS 232 interface for data logging.

Data are sent to the IBM computer in the form of distance and force values.

Data is read into a standard Microsoft Excel worksheet for analysis.

Load cell=10 N

Initial clamp separation=55 mm

Final clamp separation=25 mm

Distance sample to be deformed=30 mm

Compression speed=25 mm /1 mins.

3) Caliper Measurement Device; Mitutoyo Instruments (Japan) Model 543-601 B

The caliper is measured using a precision digital measurement device (±0.02 mm) with a circular measurement foot of 40 mm diameter that exerts a pressure of 6.2 g/cm².

Sample Preparation

The tests are performed on the final form of the product identical in all ways and preferably on the same batch of products to be worn or assessed by a consumer.

In the case of a sanitary napkin, or light incontinence device the product is removed from packaging and any release paper that may be used to maintain adhesives used to attached the article to a panty or other piece of clothing is be removed. Exposed glue surfaces (i.e. panty fastening adhesive) are rendered inactive by lightly applying a talcum powder to the adhesive surface.

Caliper Measurement

The Average caliper of the products is first determined. For products that are inherently flat the caliper at representative points (at least 5) of the product is measured to determine an average value. For products of complex shapes, such as relatively thick in the centre and relatively thin in the extremities, a smaller measurement foot on the caliper device (maintaining a measurement pressure of 6.2 g/cm²) is used and to ensure at least 10 measurement points are utilised to more accurately determine the average product thickness.

Flexibility Measurement

The product is attached vertically between the clamps of the Instron device. The clamps are so positioned to start the compression (in product cross direction) from a distance of 55 mm. The sample is compressed over a distance of 30 mm to a final clamp separation of 25 mm. The instrument details are given above.

The Instron records the clamp separation (in mm) and the force exerted to achieve this separation and send this data via an RS232 interface to an IBM computer equipped with Microsoft windows 3.1 and Microsoft Excel version 4.0. The force and distance data are loaded in to the Excel software and the average force measurements over the full 30 mm compression cycle is determined.

The measurements are performed on 10 samples of the same type to ensure a representative stiffness value to be determined for the sample under investigation.

The caliper of various core material are indicated under the core measurement table results. The results of caliper and flexibility test for an number of absorbent article test products are given under the sensory index.

Sensory Index

The sensory index is a quantitative value that reflects how a product design impacts sensory perception. The sensory index is determined from the ration of;

Effective Breathability/Product Flexibility×Product Caliper

To determine the sensory index value the following 3 tests are to be performed on the final product:
1) Effective Breathability Test.
2) Product Flexibility Test
3) Product Caliper Test

| E.g | Caliper (mm) | Flexibility (N) | VP (g/m$^2$/24 hr) | AP (l/m$^2$/s) | Effective Breathability | Sensory Index |
|---|---|---|---|---|---|---|
| 1 | 2.7 | 0.35 | zero | zero | zero | zero |
| 2 | 2.2 | 0.8 | 690 | 545 | 826 | 469 |
| 3 | 3.0 | 0.39 | 780 | 775 | 973 | 779 |
| 4 | 2.8 | 0.41 | 635 | zero | 635 | 553 |
| 5 | 2.7 | 0.34 | 580 | zero | 580 | 631 |
| 6 | ~3 | 1.5 | zero | zero | zero | zero |

VP = Vapour permeability
AP = Air permeability

VP=Vapour permeability
AP=Air permeability
Dryness Index
The dryness index is determined from the ratio of;

Effective Breathability/Product Wetness (Rewet)

To determine the dryness index value the following two tests are to be performed on the final product:
1) Effective Breathability Test
2) Product Wetness (Rewet) test.

| E.g. | Rewet (mg) | Permeability Vapour (g/m$^2$/24 hr.) | Permeability Air (l/m$^2$/sec) | Effective Breathability | Dryness Index |
|---|---|---|---|---|---|
| 1 | 50 | zero | zero | zero | zero |
| 2 | 200 | 690 | 545 | 826 | 4.1 |
| 3 | 50 | 780 | 775 | 973 | 19 |
| 4 | 50 | 635 | zero | 635 | 13 |
| 5 | 50 | 580 | zero | 580 | 12 |
| 6 | 57 | zero | zero | zero | zero |

Of the above results for the exemplified absorbent articles, absorbent article examples 1 and 6 do not meet the sensory or dryness indexes and. thus are not representative of the present invention. Examples 2–5 are representative examples of the present invention.

In preferred embodiments of the present invention the absorbent article should preferably meet at least one of the requirement of vapour permeability, air permeability, flexibility, caliper and rewet such that the article has:

a vapour permeability of greater than 100 g/m$^2$/24 hrs, preferably greater than 300 g/m$^2$/24 hrs, more preferably greater than 500 g/m$^2$/24 hrs, most preferably greater than 700 g/m$^2$/24 hrs, as defined in the absorbent article vapour permeability test.

an air permeability of greater than 100, preferably greater than 250, more preferably greater than 500, most preferably greater than 6001 l/m$^2$/s, as defined in the absorbent article air permeability test, a flexibility of less than 1.5N, preferably less than 1.0N, more preferably less than 0.8N, most preferably less than 0.5N, as defined in the flexibility test, a caliper of less than 12 mm, preferably less than 9 mm, more preferably less than 6 mm, most preferably from 5 mm to 1.5 mm, a rewet of less than 500 mg., preferably less than 300 mg., more preferably less than 200 mg., most preferably less than 100 mg as defined in the absorbent article rewet test.

What is claimed is:

1. A disposable absorbent article comprising the following elements:

a liquid pervious topsheet, an absorbent core, a breathable backsheet, and an odour control system, said absorbent core being positioned intermediate said topsheet and said backsheet, said topsheet, core and backsheet each comprising at least one layer, wherein said topsheet has a liquid retention of less than 0.22 g for a 2.0 g load in the topsheet liquid retention test, wherein said core has a caliper of less than 12 mm and has a vapour permeability of at least 200 g/m$^2$/24 hrs. as defined in the vapour permeability test and, wherein said breathable backsheet has a liquid permeability of less than 0.3 g at a 7 ml. load as defined in the liquid permeability test, wherein said elements are joined such that said absorbent article has a dryness index of greater than 0.5 and a sensory index of greater than 50.

2. A disposable absorbent article according to claim 1, wherein each said element has a wearer facing surface and a garment facing surface, each of said garment facing surfaces forming a common interface with an adjacent wearer facing surface of an adjacent element, and wherein said core and said breathable backsheet are joined across less than 40% of the common interface of said garment facing surface of said core and said wearer facing surface of said breathable backsheet.

3. A disposable absorbent article according to claim 2, wherein said core and said breathable backsheet are joined across less than 20% of said common interface of said garment facing surface of said core and said wearer facing surface of said breathable backsheet.

4. A disposable absorbent article according to claim 2, wherein said breathable backsheet element comprises at least two layers, wherein each said layer has a wearer facing surface and a garment facing surface, each of said garment facing surfaces forming a common interface with an adjacent wearer facing surface of an adjacent layer, and wherein adjacent layers are joined across less than 40% of said common interface of said adjacent layers.

5. A disposable absorbent article according to claim 4, wherein said adjacent layers are joined across less than 20% of said common interface of said adjacent layers.

6. A disposable absorbent article according to claim 2, wherein said wearer facing surface and said garment facing surface forming said common interface are joined by spiral sprayed adhesive or fusion bonding.

7. A disposable absorbent article according to claim 2, wherein said garment facing surface of said breathable backsheet has an adhesive fastening means.

8. A disposable absorbent article according to claim 7, wherein at least 60% of said garment facing surface of said backsheet is adhesive free.

9. A disposable absorbent article according to claim 7, wherein at least 80% of said garment facing surface of said backsheet is adhesive free.

10. A disposable absorbent article according to claim 1, wherein said topsheet has a liquid retention of less than 0.15 g for a 2.0 g load in the topsheet retention test.

11. A disposable absorbent article according to claim 1, wherein said core has a caliper of less than 8 mm.

12. A disposable absorbent article according to claim 1, wherein said core has a vapour permeability of greater than 600 g/m$^2$/24 hrs. as defined in the vapour permeability test.

13. A disposable absorbent article according to claim 1, wherein said breathable backsheet has a liquid permeability of less than 0.20 g for a 7 ml. load as defined in the liquid permeability test.

14. A disposable absorbent article according to claim 1, wherein said absorbent article has a sensory index of greater than 100.

15. A disposable article according to claim 1, wherein said absorbent article has a dryness index of greater than 2.

16. A disposable absorbent article according to claim 1, wherein said article has a flexibility of less than 1.5N as defined in the flexibility test.

17. An absorbent article according to claim 1, wherein said article comprises from 5 gm$^{-2}$ to 400 gm$^{-2}$ of said odour control system.

18. An absorbent article according to claim 1, wherein said odour control system comprises odour control agents selected from chelating agents, silica, zeolites, AGM, activated carbon and mixtures thereof.

19. An absorbent article according to claim 1, wherein said odour control system comprises AGM and zeolite.

20. An absorbent article according to claim 19, wherein said odour control system further comprises silica.

21. A disposable absorbent article according to claim 1 wherein said article is a sanitary napkin or a panty liner.

* * * * *